(12) United States Patent
Hunter et al.

(10) Patent No.: US 10,155,972 B2
(45) Date of Patent: Dec. 18, 2018

(54) SCREENING METHOD

(71) Applicant: IOmet Pharma Ltd., Edinburgh, Midlothian (GB)

(72) Inventors: Bill Hunter, Dundee (GB); Stuart McElroy, Dundee (GB); Alan Wise, Edinburgh (GB)

(73) Assignee: Iomet Pharma Ltd., Midlothian (GB)

( * ) Notice: Subject to any disclaimer, the term of this patent is extended or adjusted under 35 U.S.C. 154(b) by 67 days.

(21) Appl. No.: 15/105,615

(22) PCT Filed: Dec. 18, 2014

(86) PCT No.: PCT/EP2014/078567
§ 371 (c)(1),
(2) Date: Jun. 17, 2016

(87) PCT Pub. No.: WO2015/091862
PCT Pub. Date: Jun. 25, 2015

(65) Prior Publication Data
US 2017/0009271 A1    Jan. 12, 2017

(30) Foreign Application Priority Data
Dec. 20, 2013  (GB) .................................. 1322673.3

(51) Int. Cl.
*C12Q 1/26*    (2006.01)
*C12Q 1/48*    (2006.01)

(52) U.S. Cl.
CPC .................. *C12Q 1/26* (2013.01); *C12Q 1/48* (2013.01); *G01N 2333/90241* (2013.01); *G01N 2500/04* (2013.01); *G01N 2500/20* (2013.01)

(58) Field of Classification Search
CPC combination set(s) only.
See application file for complete search history.

(56) References Cited

FOREIGN PATENT DOCUMENTS

| WO | WO2004093871 A1 | 11/2004 |
|---|---|---|
| WO | 2006005185 A1 | 1/2006 |
| WO | 2006056304 A2 | 6/2006 |
| WO | 2008143668 A2 | 11/2008 |

OTHER PUBLICATIONS

Alexander Muller, Pendergrass et al (Indoleamine 2,3-dioxygenase in cancer: targeting pathological immune tolerance with small-molecule inhibitors (Oncologic, Endocrine & Metabolic p. 831-849, 2005. (Year: 2005).*

Muller, A.J., et al., Indoleamine 2,3-dioxygenase in cancer: Targeting pathological immune tolerance with small-molecule inhibitors, Expert Opinion on Therapeutic Targets, 2005, pp. 831-849, vol. 9(4).

* cited by examiner

*Primary Examiner* — Kagnew H Gebreyesus
(74) *Attorney, Agent, or Firm* — Yong Zhao; Catherine D. Fitch

(57) ABSTRACT

Provided is a high-throughput coupled enzyme method of screening for a tryptophan-2,3-dioxygenase (TDO) inhibitor compound and/or an indoleamine-2,3-dioxygenase (IDO) inhibitor compound, which method comprises: (a) reacting tryptophan with isolated IDO and/or isolated TDO in the presence of a test compound to form N-formylkynurenine; (b) reacting N-formylkynurenine from step (a) with isolated kynurenine formamidase to form kynurenine; and (c) detecting the kynurenine produced in step (b) and determining whether the test compound is a TDO and/or an IDO inhibitor compound or not from the presence or absence or quantity of the detected kynurenine, wherein step (a) is conducted in the presence of a reducing system suitable for converting IDO and/or TDO from the $Fe^{3+}$ to the $Fe^{2+}$ state, and which does not prevent the formation of kynurenine in step (c).

20 Claims, 8 Drawing Sheets

SCREENING METHOD

CROSS REFERENCE TO RELATED APPLICATIONS

This application is a U.S. National Phase application under 35 U.S.C. § 371 of PCT Application No. PCT/EP2014/078567 filed Dec. 18, 2014, which claims priority from GB Application Serial No. 1322673.3, filed Dec. 20, 2013.

The present invention relates to a method of screening for a tryptophan-2,3-dioxygenase (TDO) inhibitor compound and/or an indoleamine-2,3-dioxygenase (IDO [IDO1 or IDO2]) inhibitor compound, and to compounds obtainable or obtained according to these methods. The inhibitors uncovered by the method of the invention may be used in pharmaceutical compositions, and in particular pharmaceutical compositions for treating a cancer, an inflammatory condition, an infectious disease, a central nervous system disease or disorder and other diseases, conditions and disorders.

Tryptophan Metabolism

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to supress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolising enzyme extrahepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO−/− knockout mice also display enhanced inflammatory-mediated colon carcinogenesis and exhibit resistance to inflammation-driven lung and skin cancers (Chang et al., 2011; Yan et al., 2010).

The TDO−/− knockout mouse appears phenotypically normal. However, the TDO knockout mice have a 9-fold increase in the plasma concentration of L-Trp, while IDO−/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO−/− mice show increased neurogenesis in the hippocampus and subventricular zone during adulthood (Funakoshi et al., 2011).

Immuno-Modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of TDO and/or IDO have utility in a wide range of indications, including Infectious diseases, cancer, neurological conditions and many other diseases.

Infectious Diseases and Inflammation

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor IMT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs., et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and Immunity to Gut Bacteria

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+ T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-Induced Hypotension

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

CNS Disorders

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic Lateral Sclerosis

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites with in the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's Disease

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric Disorders and Pain

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β(Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's Disease

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3HK and QUIN. 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer

It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO

TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with anti-CTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases

Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health

Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and Abortion

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al., 1998). Accumulating evidence indicates that IDO production and normal function at the foetal-maternal interface may play a prominent role in pregnancy tolerance (Durr and Kindler., 2013). Therefore, an IDO/TDO inhibitor could be used as a contraceptive or abortive agent.

On the above basis, the inventors have determined that a strong rationale exists for the therapeutic utility of drugs which block the activity of TDO and or IDO, in treating the above-mentioned diseases, conditions and disorders. Accordingly, there exists a need for a method of screening for such TDO and/or IDO inhibitors.

It has been known to detect such inhibitors in the past by monitoring the breakdown of tryptophan in which IDO and TDO play a significant part. This has been achieved by directly measuring N-formylkynurenine production by reading an absorbance increase at 321 nm or at 254 nm.

However, this methodology is subject to significant background interference effects due to the high levels of absorbance typically demonstrated by conjugated molecules at this wavelength. Hence, this limits the use of such methodology for screening libraries of organic compounds in order to identify modulators of TDO and IDO activity as the false-positive hit rates due to high background compound interference can be very high.

Alternatively, screening methods have been devised in which N-formylkynurenine is converted to kynurenine by measuring kynurenine levels in a chemically-coupled system which converts N-formylkynurenine to kynurenine following the addition of 6M trichloroacetic acid (TCA) or 1M sodium hydroxide (NaOH) and heating to 50° C. and centrifugation to remove precipitates. Kynurenine is subsequently quantified by LC/MS or by spectrophotometric means (described in WO2011/045341, WO2008/143668A and US2006/0110371A) following the addition of Ehrlich's reagent and subsequent formation of a Schiff's base by measuring fluorescence at 475-530 nm or absorbance at 470-490 nm. However, this methodology is also not amenable to high-throughput screening (HTS) from both a safety and practical perspective due to the use of harsh conditions (high concentration acid or base, high temperature) and multiple reaction steps. The use of acid or base, the necessity to heat assay plates to 50° C. and centrifugation steps also restricts the suitability of this assay procedure for adaptation to laboratory robotics and automation, a key requisite to enable high-throughput screening.

Screening methods that employ kynurenine formamidase to convert N-formylkynurenine to kynurenine have also been developed. These screening methods have typically employed liver homogenate or liver slices in in vitro methods in order to ensure that the coupled enzyme system (a system in which TDO, IDO and kynurenine formamidase are all simultaneously present and able to perform their function) is as close to the in vive system as possible. For example, such assays are disclosed in Young et al., Biochemical Pharmacology, 1978, 27, 763-767 and J. Siefert, Journal of Chromatography, 614 (1993), 227-231. However, these assays are also not amenable to high-throughput screening due to the methodologies required for using primary liver homogenates or slices.

IDO and TDO are haem-dependent, intracellular dioxygenases, and are only active in the reduced ferrous ($Fe^{2+}$)-bound state. As a consequence in order to reconstitute enzymatic activity on the isolated proteins in vitro, both TDO and IDO require an exquisitely precise reducing environment. This allows such the enzymes to cycle from the $Fe^{3+}$ state produced at the end of the enzymatic mechanism back to the $Fe^{2+}$ active state. The maintenance of this precise reducing environment is present within intact cells (see the assays in Young et al. and Siefert above) and is demonstrated by many cellular assay systems in the literature around TDO and IDO (see Dolusic et al. J. Med. Chem. 2011, 54, 5320-5334 and Dolusic et al. Eur. J. Med. Chem. 2011, 46, 3058-3065). This reducing environment is easily lost if the cells are disrupted. Cellular maintenance of reductive capacity is believed to be essential for many mammalian enzymes: this has been achieved in many ways, e.g. NADH/NAD+ and NADPH/NADP+ ratios amongst others. Furthermore, the endogenous reducing cofactors required for maintaining IDO and TDO activity have yet to be identified, although, some reports have demonstrated that cytochrome b5 is capable of reducing $Fe^{3+}$-IDO to support catalytic activity (Maghzal et al. J. Biol. Chem. 2008, 283, 12014-12025; Vottero et al. FEBS Lett. 2006, 580, 2265-2268). The belief that there is a need to employ intact cells, in order to re-create a suitable reducing system, has provided a barrier to the development of a HTS assay for IDO/TDO using isolated enzymes.

A hierarchy is accepted in the field that tissue/cellular homogenates offer the next best option to intact cells for measuring enzymatic activity as they contain many of the cellular enzymes present involved with cellular redox control. However, this reducing control is lost once moving to purified/recombinant enzymes and as such must be re-established artificially in vitro to measure the activity of enzymes dependent on a reducing environment. This is exactly the case with TDO/IDO and has been demonstrated in a number of publications whereby a combination of methylene blue and ascorbic acid are used to provide the necessary reducing environment (Takikawa et al., J. Biol. Chem. 1988, 263, 2041-2048, Lu et al Biochemistry 2010, 49, 5028-5034 and Basran et al., Biochemistry 2008, 47, 4752-4760). Starting with intact tissue slices, the measurement of kynurenine has been described from liver slices (TDO) after separation by HPLC (Seifert et al.). Whilst sensitive, this method is clearly not scalable for routine compound high-throughput screening purposes, notwithstanding that the authors stress significant advantages over homogenates and purified enzymes (most likely as they consider that the architecture of the liver cells remains intact thereby keeping the reducing system more physiological). This is demonstrated further by Meininger et al. Biochimica et Biophysica Acta 2011, 1814, 1947-1954, who utilised a chemical reducing system composed of ascorbate and methylene blue in an attempt to configure an HTS-compatible assay system for screening for inhibitors of IDO. However, this assay system also required the subsequent addition of strong base (1M NaOH) in order to hydrolyse N-formylkynurenine to kynurenine. The same laboratory also reconstituted a more physiological in vitro reducing system for measuring enzymatic IDO activity by incubating recombinant IDO with cytochrome b5 and NADPH-cytochrome P450 reductase (Pearson et al. Biochemistry 2010, 49, 2647-2656). The authors speculated that the discovery of this potential natural electron transfer partner capable of reducing IDO and supporting its activity may enable a more suitable system for identifying inhibitors. These significant attempts to establish robust HTS-compatible assays using purified recombinant IDO by optimising the reductive environment to better reflect the in vivo situation have not been effective as evidenced by a recent patent literature review by Dolusic and Frederick, in Expert Opin. Ther. Patents 2013, 23, 1367-1381, and are completely in line with the observations by Seifert et al., who acknowledged the difficulty in producing sufficiently active haem-containing TDO that one could use to determine inhibitory activity of compounds in screening collections. This highlights the complexity and difficulty in establishing conditions around the purified enzymes, such that one can use the assays for modern HTS purposes.

Importantly, the coupling of both recombinant TDO and/or IDO with recombinant kynurenine formamidase has never been demonstrated in the literature. The barrier to development of a TDO/IDO screen using isolated enzyme is even greater when a coupled system is considered, in which isolated kynurenine formamidase is also employed. The reducing system needed to support the TDO/IDO enzyme activity must also not interfere with the activity of kynurenine formamidase. To date, a reducing system capable of satisfying both requirements has not been identified. In fact, there has been no known attempt to find such a system, since it has not been considered likely to be successful. As has been said, Seifert et al. have stressed significant advantages of liver slices over homogenates and purified enzymes.

However, an HTS screen is still desired. As recently discussed by two experts in this field, Dolusic and Frederick, in Expert Opin. Ther. Patents 2013, 23, 1367-1381, despite intensive efforts and the large variety of potential inhibitors screened so far, the number of active scaffolds remains limited with only two confirmed inhibitors (from Incyte Corp. and NewLink Genetics Corp.) in the clinic at either TDO or IDO. This dearth of confirmed inhibitors maybe a direct consequence of the aforementioned limitations of existing assay methodologies employed in screening IDO and TDO.

In summary, up to present, it has not been possible to develop an assay for TDO and/or IDO inhibitors that is suitable for high-throughput screening. Assays which might be suitable are those which employ enzymes which have been isolated (and/or purified), such as recombinant enzymes, and so are more easily processed in a high-throughput system. However, up to present it has not been possible to create an efficient coupled enzyme system using isolated enzymes, due to the difficulty in re-creating the reaction conditions found either in vivo or in liver cells in vitro. Particular problems have arisen in re-creating the correct reducing environment for isolated TDO and IDO to function. In assays where kynurenine formamidase is coupled with TDO and/or IDO, further problems include ensuring that the conditions suitable for TDO and/or IDO are also suitable for the efficient functioning of the kynurenine formamidase.

The inventors have determined to solve the problems set out above, and have recognised that there is a need for alternative and improved screening methods for detecting compounds which are IDO and/or TDO inhibitors. In particular, the inventors have determined that there is a need for high-throughput screening methods, which may employ a coupled enzyme system, and/or may employ isolated and/or purified TDO and/or IDO and/or kynurenine formamidase.

Thus, it is an aim of the present invention to provide a high-throughput coupled enzyme method for screening for TDO inhibitors or IDO inhibitors, and in particular screening for TDO and IDO inhibitors for use in medicine. It is a further aim to provide pharmaceutical compositions comprising inhibitors obtainable by such screening methods, and in particular to provide such compounds and pharmaceutical compositions for treating a cancer, an inflammatory condition, an infectious disease, a central nervous system disease or disorder and other diseases, conditions and disorders.

Accordingly, the present invention provides a high-throughput coupled enzyme method of screening for a tryptophan-2,3-dioxygenase (TDO) inhibitor compound and/or an indoleamine-2,3-dioxygenase (IDO) inhibitor compound, which method comprises:
(a) reacting tryptophan with isolated IDO and/or isolated TDO in the presence of a test compound to form N-formylkynurenine;
(b) reacting N-formylkynurenine from step (a) with isolated kynurenine formamidase to form kynurenine; and
(c) detecting the kynurenine produced in step (b) and determining whether the test compound is a TDO and/or an IDO inhibitor compound or not from the presence or absence or quantity of the detected kynurenine,
wherein step (a) is conducted in the presence of a reducing system suitable for converting IDO and/or TDO from the $Fe^{3+}$ to the $Fe^{2+}$ state, and which does not prevent the formation of kynurenine in step (c).

In the context of the present invention, the term "high throughput" screening has its normal meaning in the art and refers to the well-known term in the field of drug discovery, especially in the pharmaceutical industry. It typically refers to screening processes employing automation to assay the biological or biochemical activity of a large number of drug-like compounds.

In the context of the present invention a "coupled enzyme" method is a method in which two or more enzymes are present simultaneously and the product of a first reaction is the substrate for a second. Thus, in the present assay, the coupled system may involve action of TDO followed by action of kynurenine formamidase, or may involve action of IDO followed by action of kynurenine formamidase.

In the context of the present invention, "isolated" may mean a form of TDO or IDO or kynurenine formamidase that has been isolated from a natural source, or it may mean a form of TDO or IDO or kynurenine formamidase that has been synthesised artificially, such as recombinant TDO or recombinant IDO or recombinant kynurenine formamidase. In each case the "isolated" enzyme may preferably have been purified.

In the context of the present invention, "does not prevent" may mean does not substantially interfere with, does not substantially inhibit, does not substantially reduce the formation of, or the like.

Advantageously the present inventors have developed a functional HTS coupled enzymatic assay system for identification of TDO and/or IDO inhibitors from large industrial screening libraries. Consideration of the precise in vitro conditions has been given due to the fact that both TDO and IDO activity were known to be extremely sensitive to reducing conditions, and these problems have now been overcome without substantially detrimentally affecting the activity of kynurenine formamidase. Furthermore, the enzymatically-coupled assay system that the present inventors have developed does not require the addition of a complex endogenous reducing system such as cytochrome b5 and NADPH-cytochrome P450 reductase. The enzymatically coupled assay methodology of the invention circumvents the limitations of current methods for high-throughput screening.

Since the assay of the present invention is a coupled assay, it involves converting N-formylkynurenine to kynurenine. This has three significant advantages over existing published technology measuring modulation of IDO and TDO activities for screening purposes:

Firstly, it allows detection of kynurenine either by direct absorbance or fluorescence-based read-outs at wavelengths that are typically much less subject to interference effects by organic test agents that are observed at the wavelength used for direct detection of N-formylkynurenine (321 nm). A direct consequence of this is a lower false positive hit rate and hence more facile detection of true inhibitors.

Secondly, it provides an enzymatic alternative to coupling the activities of IDO and TDO to the formation of kynurenine, hence removing the need for using harsh conditions (concentrated acid or base, heating assay plates to 50° C.), centrifugation and minimising the number of reaction steps in the assay, all of which are critical for the success of adapting an assay onto automated robotic screening platforms used for high-throughput screening. Crucially, this industrialises the TDO/IDO screening process by removing manual steps and enabling screening of libraries with the large numbers of compounds typically used in industrial drug discovery.

Thirdly, the formamidase-coupled assay system provides a homogeneous assay system with a highly amplified signal window (FIG. 3) compared to the direct method of N-formylkynurenine measurement (FIG. 4). This increase in sensitivity is crucial to identifying weakly active hit molecules from large compound collections during high-throughput screening campaigns. This is an unexpected advantage, and has contributed to the inventors discovering large numbers of TDO/IDO inhibitors which are under investigation as potential pharmaceutical candidates. The high sensitivity of the assay is surprising, and the benefit of the identification of a large number of candidates (in a field with a previous dearth of such candidates) is significant.

Taken together, the use of formamidase as the coupling enzyme to bridge between the activities of IDO and TDO and the formation of the easily detectable product kynurenine makes these assays amenable to miniaturisation and for use in industrial, non-manual ultra-high-throughput screening processes. Furthermore, because of the coupled nature of the new method, it provides a significant increase in assay signal window over the direct assay system which measures N-formylkynurenine. Thus crucially the new method is a more sensitive system for detecting modulators of IDO and TDO activity enabling the detection of weakly acting inhibitory hit molecules with IC50 values typically >10 μM consistent with its suitability for high-throughput screening purposes.

The invention will now be explained in more detail, by way of example only, with reference to the following Figures.

FIG. 1 shows a schematic diagram of tryptophan catabolism along the KP (from "The Kynurenine Pathway in Brain Tumour Pathogenesis", Adam et al., 2012, Cancer Res 72:5649-57).

FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6):1211-27.

Figure 1:
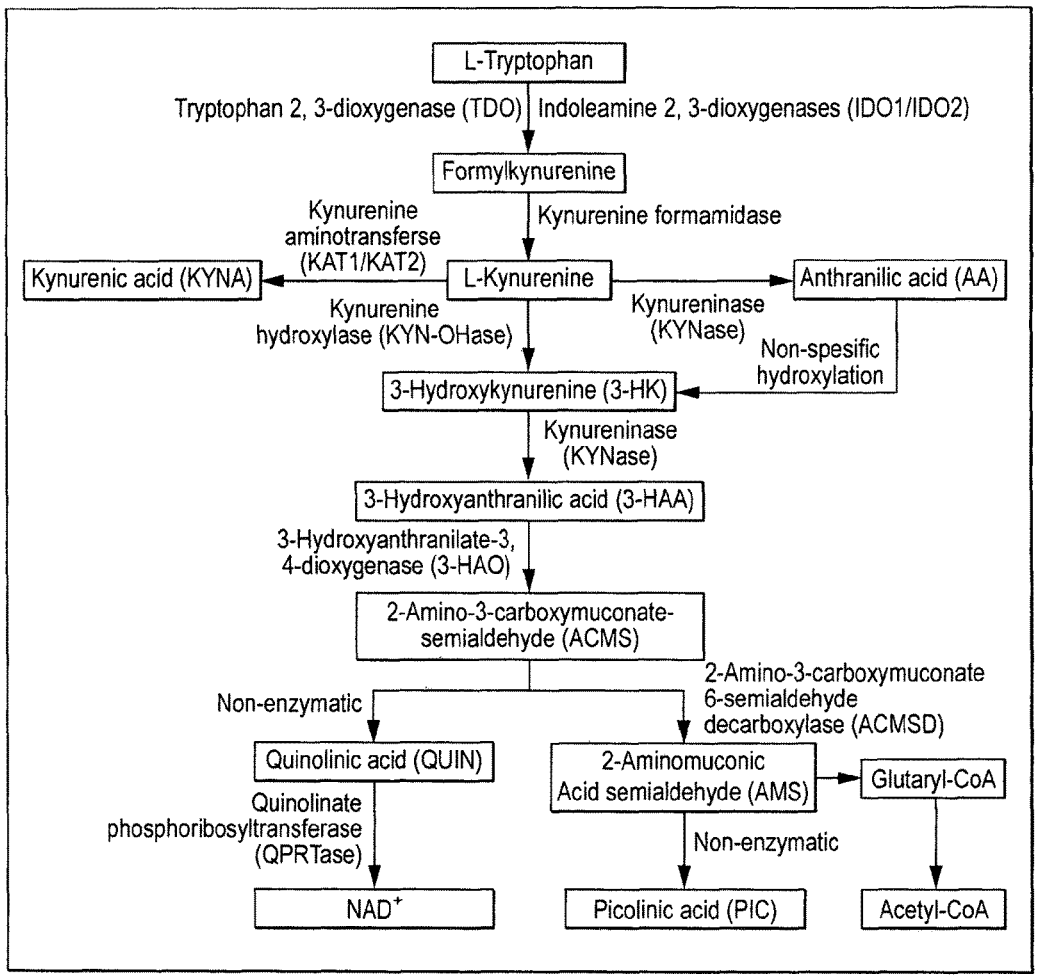
Figure 2:
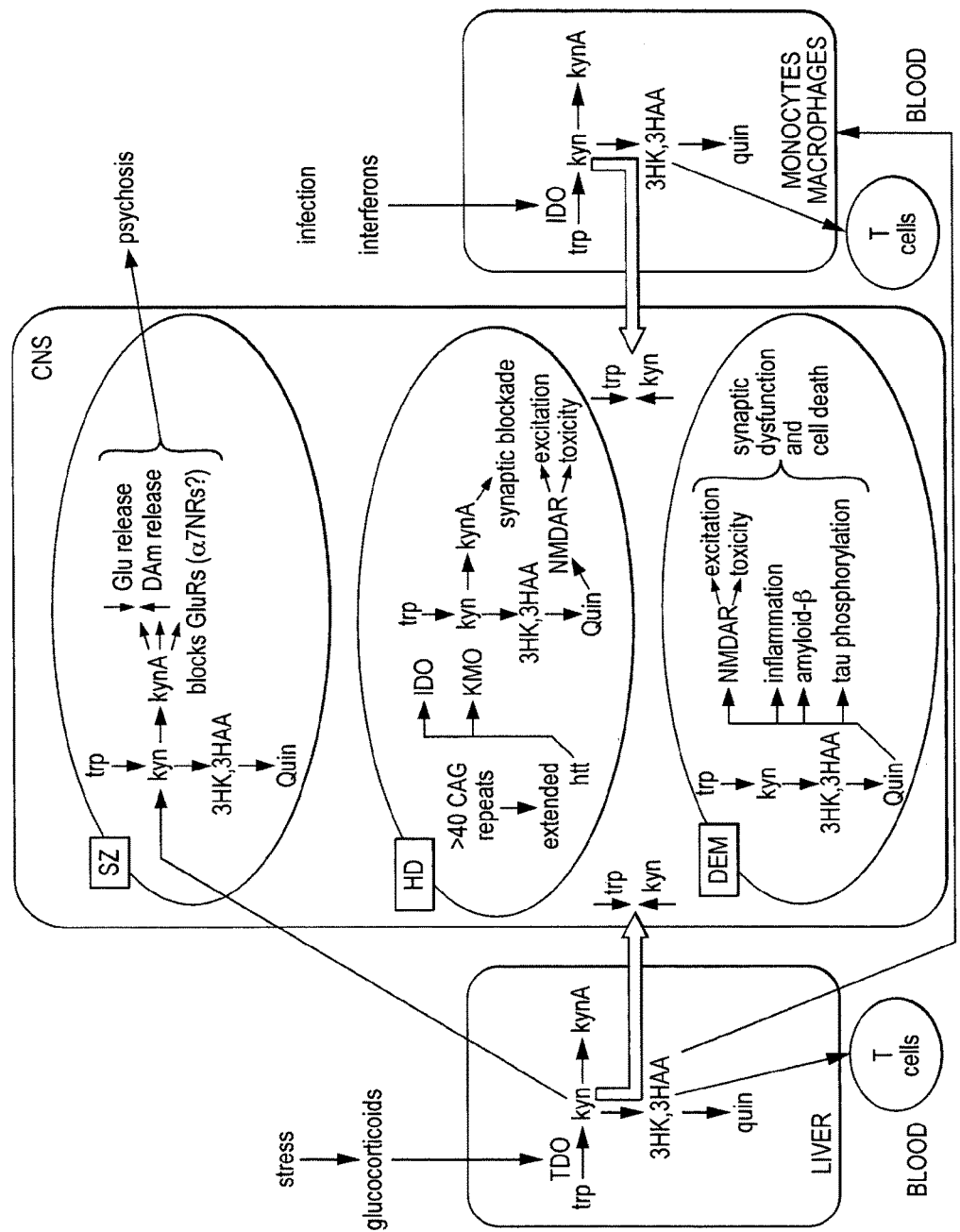
Figure 3:
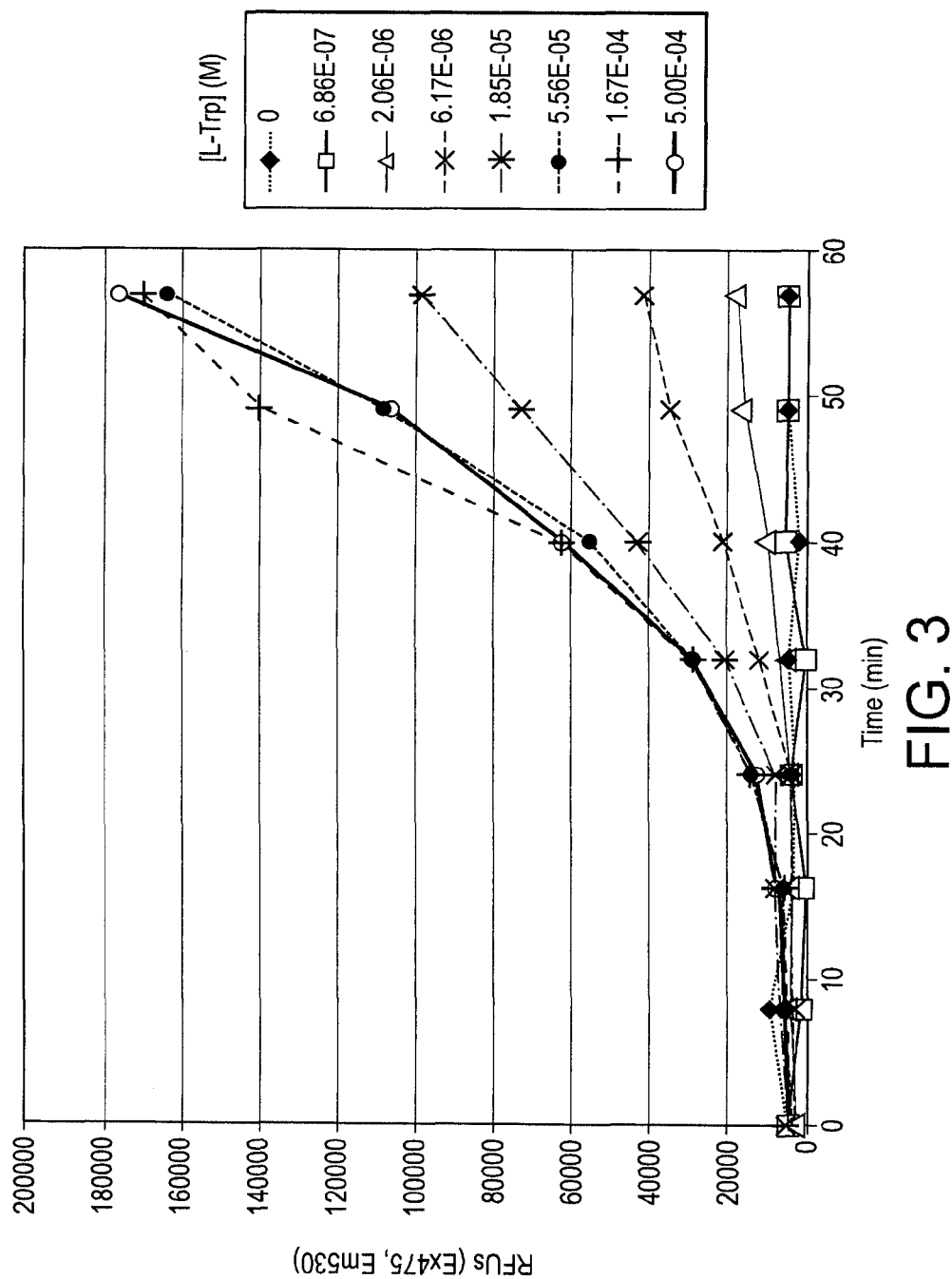
FIG. 3 shows a highly amplified signal window as depicted by fluorescence unit change in the coupled assay for human IDO across a range of substrate (L-Trp) concentrations.
Figure 4:
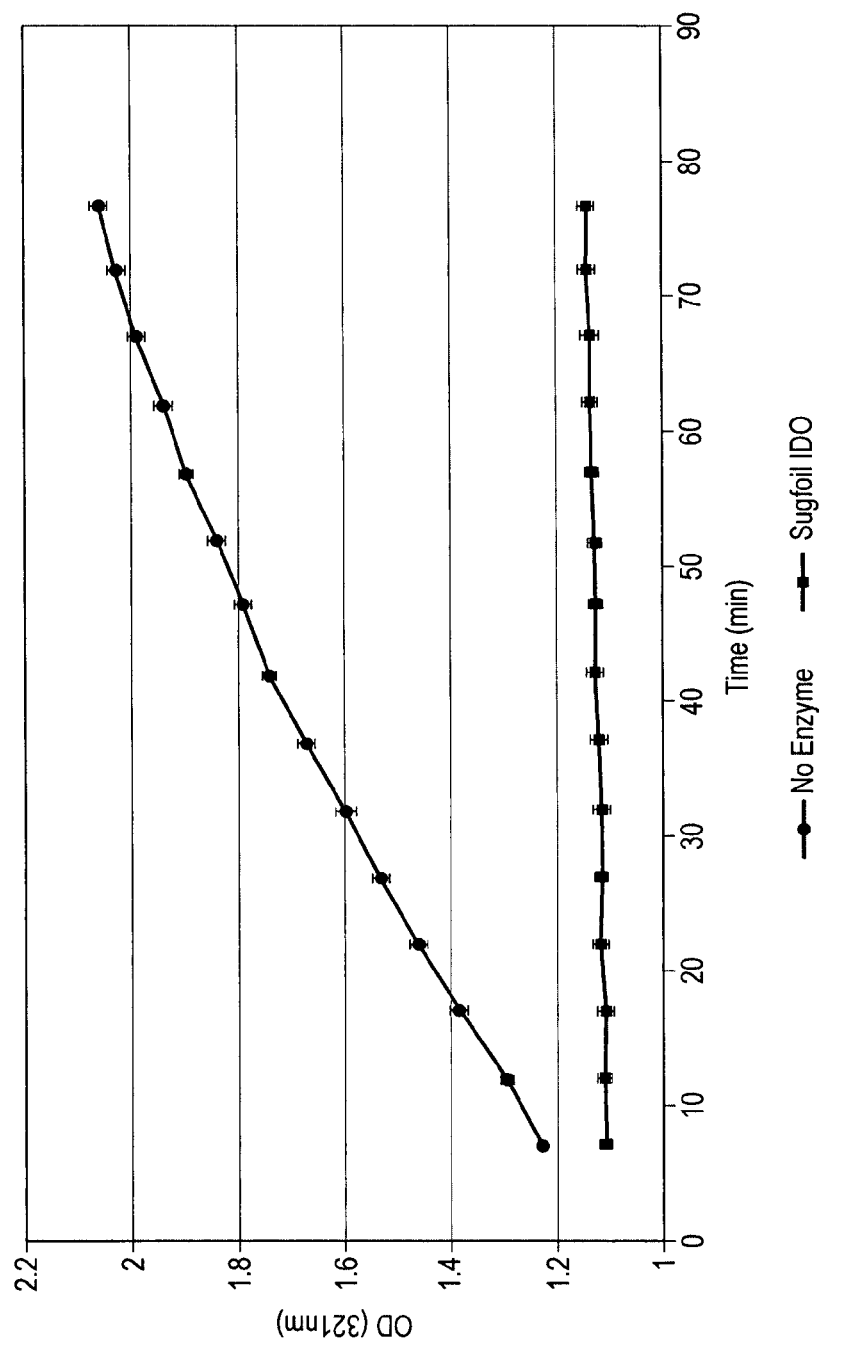
FIG. 4 shows a limited signal window as depicted by absorbance increase at 321 nm in the direct biochemical assay for human IDO.

The invention will now be described in more detail.

As has been described, the invention relates to a high-throughput coupled enzyme method of screening for a tryptophan-2,3-dioxygenase (TDO) inhibitor compound and/or an indoleamine-2,3-dioxygenase (IDO) inhibitor compound, which method comprises:
(a) reacting tryptophan with isolated IDO and/or isolated TDO in the presence of a test compound to form N-formylkynurenine;
(b) reacting N-formylkynurenine from step (a) with isolated kynurenine formamidase to form kynurenine; and
(c) detecting the kynurenine produced in step (b) and determining whether the test compound is a TDO and/or an IDO inhibitor compound or not from the presence or absence or quantity of the detected kynurenine, wherein step (a) is conducted in the presence of a reducing system suitable for converting IDO and/or TDO from the $Fe^{3+}$ to the $Fe^{2+}$ state, and which does not prevent the formation of kynurenine in step (c).

The detection of kynurenine is not especially limited, and may be performed using any suitable means. However, in more advantageous embodiments of the invention it is carried out by direct absorbance or by fluorescence. Typically the absorbance wavelength is from 480-500 nm and typically the fluorescence wavelength is from 475-530 nm. The screening method may test only for the presence or absence of kynurenine (typically according to a threshold level, such as a threshold absorbance or fluorescence signal at the appropriate wavelength, below which absence is assumed), or alternatively the quantity of kynurenine may be determined (typically according to the strength of the absorbance or fluorescence signal at the appropriate wavelength).

In the screening method of the invention, it will be clear that the smaller the quantity of kynurenine observed, the greater the inhibitory effect of the test compound. Therefore, typically in step (c) the inhibitor function of the test compound is determined in inverse proportion to the quantity of kynurenine measured.

A determination that a particular test compound is an inhibitor is typically made if the kynurenine level measured in the presence of the test compound is lower than the kynurenine level measured in an equivalent method in the absence of the test compound.

The measurement of the presence or absence or quantity of kynurenine may be made using any suitable process. However, typically step (c) comprises a step of measuring the presence or absence or quantity of kynurenine by reacting the product of step (b) with Ehrlich's reagent and measuring the fluorescence intensity of the product.

In the present method, the nature of the IDO, TDO and/or kynurenine formamidase is not especially limited. However, in typical embodiments these reagents are synthetic, and are recombinantly produced. Typically, human IDO and/or human TDO are employed. In some embodiments, kynurenine formamidase from *drosophila* is advantageous.

The present invention employs a reducing system suitable for converting IDO and/or TDO from the $Fe^{3+}$ to the $Fe^{2+}$ state. The reducing system should be suitable for recycling the TDO and/or IDO enzyme, but should not unduly inhibit the activity of the kynurenine formamidase. Typically the reducing system comprises a reducing agent and an electron transport agent (which may be an electron carrier and/or an electron donor). Suitable reducing agents include, but are not limited to ascorbic acid, tris(2-carboxyethyl)phosphine (TCEP), and dithionite (the dithionite anion, $[S_2O_4]^{2+}$ with any suitable cation, such as $Na^+$). Suitable electron transport agents include, but are not limited to, methylene blue. Such agents are typically applied in the 0.1-20 mM range.

The invention further provides a method for screening for an agent for treating a disease, a condition, and/or a disorder, which method comprises a method as defined above. The disease, condition or disorder is not especially limited, provided that it is beneficially affected by treatment with a TDO or IDO inhibitor compound, agent or composition. Typically, the disease condition and/or disorder is selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts, which compound is a compound as defined in any preceding claim.

Typically, the inflammatory condition is a condition relating to immune B cell, T cell, dendritic cell, natural killer cell, macrophage, and/or neutrophil dysregulation. Further typically, when the agent is an IDO inhibitor the cancer is preferably a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, *Proteus* syndrome, and *Proteus*-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma), and preferably a cancer selected from acute myeloid leukemia (AML), a small-cell lung cancer, a melanoma, an ovarian cancer, a colorectal cancer, a pancreatic cancer, an endometrial cancer, and a skin papilloma. Also typically, when the agent is a TDO inhibitor the cancer is preferably a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, *Proteus* syndrome, and *Proteus*-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma), and preferably wherein the cancer is a cancer selected from a glioma, and a hepatocellular carcinoma.

Advantageously, the infectious disease is selected from a bacterial infection and a viral infection, preferably a gut infection, sepsis, and sepsis induced hypotension.

In other typical embodiments, the central nervous system disease or disorder is selected from amyotrophic lateral sclerosis (AML), Huntington's disease, Alzheimer's disease, pain, a psychiatric disorder, multiple sclerosis, Parkinson's disease, and HIV related neurocognitive decline.

When the disease or disorder is one relating to female reproductive health, it is typically selected from endometriosis, or relates to contraception or abortion.

The invention also provides a tryptophan-2,3-dioxygenase (TDO) and/or an indoleamine-2,3-dioxygenase (IDO) inhibitor compound or agent obtainable or obtained according to a method as defined above.

Further provided is a pharmaceutical composition which composition comprises a compound as defined above.

Also provided is a method for treating a disease, a condition, and/or a disorder, which method comprises administering a compound or agent as defined above and/or a composition as defined above to a patient. Typically the patient is a mammal, and more typically the patient is human.

The invention will now be described in more detail, by way of example only, with reference to the following specific embodiments.

EXAMPLES

Example 1—Protein Purification

Human IDO Protein Purification

N-terminally His-tagged full length human IDO protein was overexpressed in *E. coli*. Frozen cell pellets were thawed in buffer A (20 mM sodium phosphate, pH 8.0, 500 mM NaCl, 10 mM imidazole, 5 mM β-mercaptoethanol and protease inhibitors) and incubated for 30 min on ice in the presence of lysozyme. Cells were disrupted by sonication and insoluble material was pelleted by centrifugation. His-tagged protein was purified by metal ion affinity chromatography (IMAC) using a Ni-sepharose column and eluted in buffer A containing 500 mM imidazole. Fractions containing eluted protein were subjected to size exclusion chromatography on a column equilibrated in 25 mM MES, pH 6.5, 150 mM KCl.

Human TDO Protein Purification

N-terminally His-tagged full length human TDO protein was overexpressed in *E. coli*. Frozen cell pellets were thawed in buffer A (20 mM sodium phosphate, pH 8.0, 500 mM NaCl, 10 mM imidazole, 5 mM β-mercaptoethanol and protease inhibitors) and incubated for 30 min on ice in the presence of lysozyme. Cells were disrupted by sonication and insoluble material was pelleted by centrifugation. His-tagged protein was purified by metal ion affinity chromatography (IMAC) using a Ni-sepharose column and eluted in buffer A containing 500 mM imidazole. Fractions containing eluted protein were subjected to size exclusion chromatography on a column equilibrated in 50 mM $KH_2PO_4$, pH 7.0, 300 mM NaCl, 0.5 mM EDTA, 0.5 mM EGTA.

Drosophila Kynurenine Formamidase Protein Purification

N-terminally His-tagged full length *drosophila* kynurenine formamidase was overexpressed in *E. coli*. Frozen cell pellets were thawed in buffer A (20 mM sodium phosphate, pH 8.0, 500 mM NaCl, 10 mM imidazole, 5 mM 3-mercaptoethanol and protease Inhibitors) and incubated for 30 min on ice in the presence of lysozyme. Cells were disrupted by sonication and insoluble material was pelleted by centrifugation. His-tagged protein was purified by metal ion affinity chromatography (IMAC) using a Ni-sepharose column and eluted in buffer A containing 500 mM imidazole. Fractions containing eluted protein were subjected to size exclusion chromatography on a column equilibrated in 50 mM $NaH_2PO_4$, pH 7.8, 150 mM NaCl, 5% glycerol.

Example 2—Exemplary Compounds for TDO and IDO Inhibition

TDO inhibitors, 680C91 and LM10, and IDO inhibitors, NewLink 1 and compound Incyte 1 as referenced by Salter et al., (1995) Biochem. Pharmacol. 49, 1435-1442; Dolusic et al., (2011) J. Med. Chem. 54, 5320-5334; Mautino et al., (2013) AACR Poster Abstract 491; Yue et al., (2009) J. Med. Chem. 52, 7364-7367, respectively, were chosen for testing for activity at TDO and IDO in the biochemical coupled assays and cell-based assays.

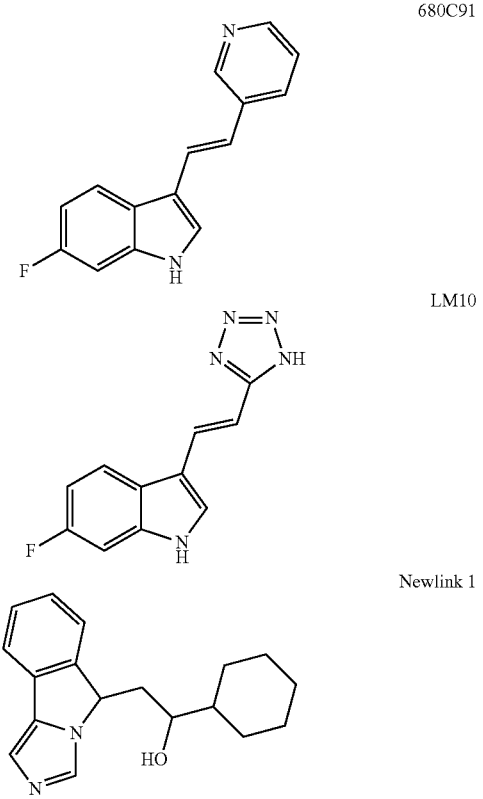

680C91

LM10

Newlink 1

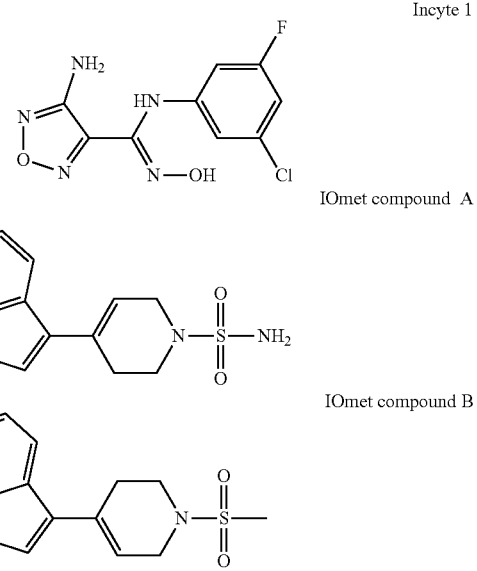

Incyte 1

IOmet compound A

IOmet compound B

Example 3—Screening Assays

The exemplary compounds of the invention (LM10, NewLink 1, Wellcome 680C91, Incyte 1, IOmet A and IOmet B), as highlighted above, were tested to determine their effect as TDO and/or IDO inhibitors in the high-throughput assay of the invention compared with literature quoted activities for these compounds. A TDO and IDO biochemical coupled assay was employed, using the screening method of the invention, which utilised recombinantly produced and purified TDO and IDO enzymes in combination with the enzyme kynurenine formamidase, obtained as explained above. This coupled enzyme system allowed conversion of N-formylkynurenine produced by TDO or IDO activity to kynurenine which was then quantified by fluorescence following addition of Erhlich's Reagent. The protocol for this is set out below.

TDO Coupled Biochemical Assays

Figure 5:
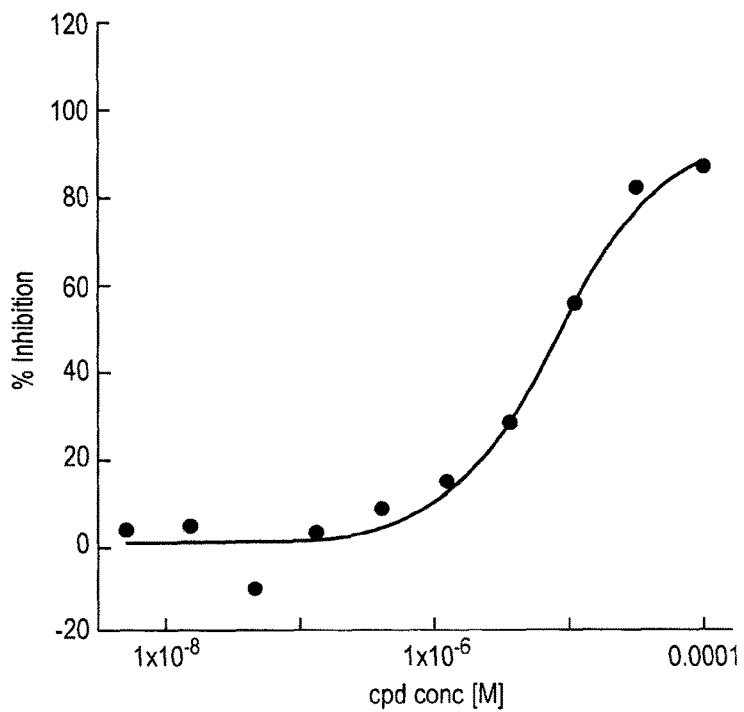
FIG. 5 shows concentration-dependent inhibition of human TDO by compound 680C91 in the coupled assay.
Figure 6:
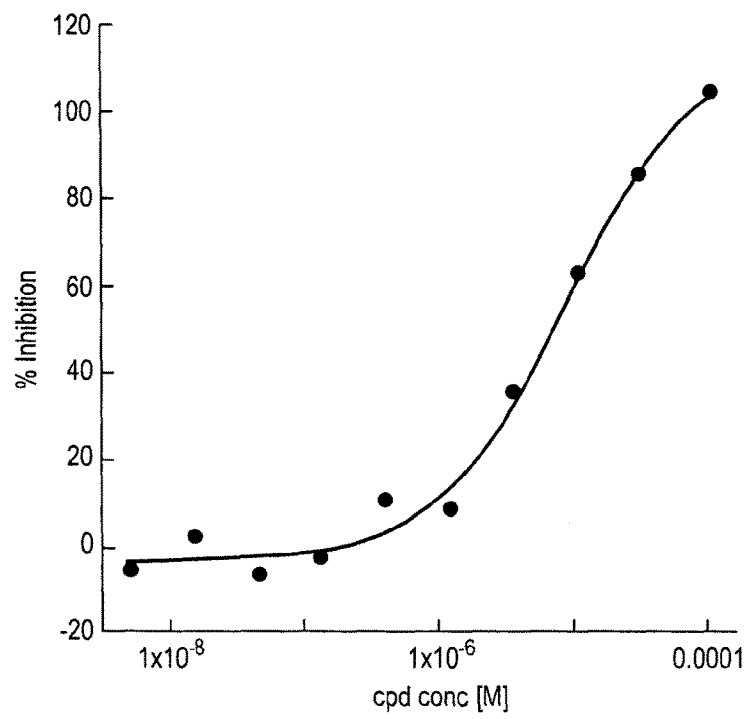
FIG. 6 shows concentration-dependent inhibition of human TDO by compound LM10 in the coupled assay.

In two separate assays, 2.5 µg/µl of human TDO protein was pre-incubated for 10 minutes at RT with test compounds 680C91 and LM10 in the presence of 50 mM $KH_2PO_4$, pH 7.0, 0.5 mM EDTA, 0.5 mM EGTA, 0.05% Triton X-100, 20 mM ascorbate, 500 U/ml catalase, 10 µM methylene blue at RT in a 384 well plate. 0.05 µg/µl kynurenine formamidase (*drosophila*) and 330 µM L-tryptophan were added and the assays were incubated at room temperature (RT) for 17 min. Assays were stopped and the level of kynurenine was determined by incubation with Ehrlich's reagent to a final concentration of 1.33% at RT for 5 min. Fluorescence intensity was read at 475 nm/530 nm. The results are depicted in FIG. 5 and FIG. 6 respectively.

IDO Coupled Biochemical Assays

Figure 7:
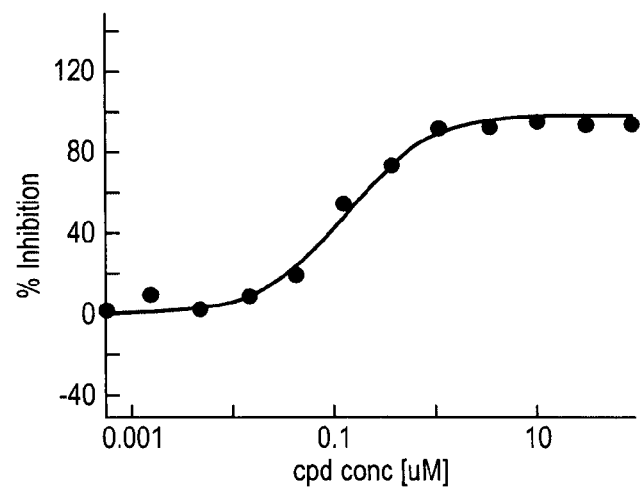
FIG. 7 shows concentration-dependent inhibition of human IDO by compound Newlink 1 in the coupled assay.
Figure 8:
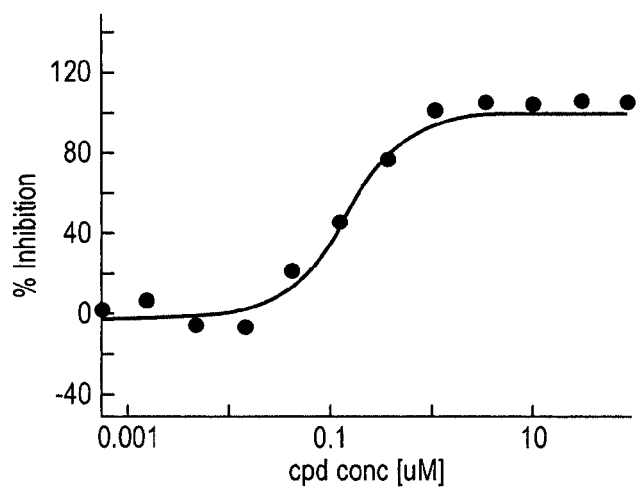
FIG. 8 shows concentration-dependent inhibition of human IDO by Incyte 1 in the coupled assay.
Figure 9:
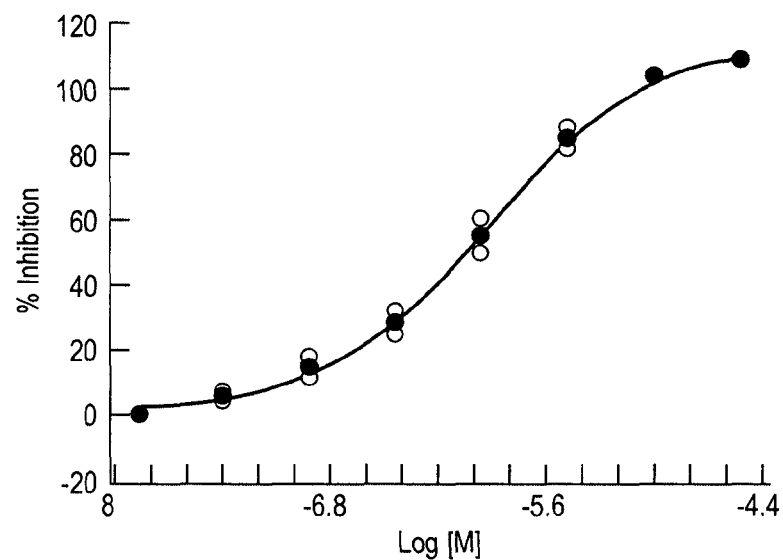
FIG. 9 shows inhibition of kynurenine production in A172 cells by compound 680C91.
Figure 10:
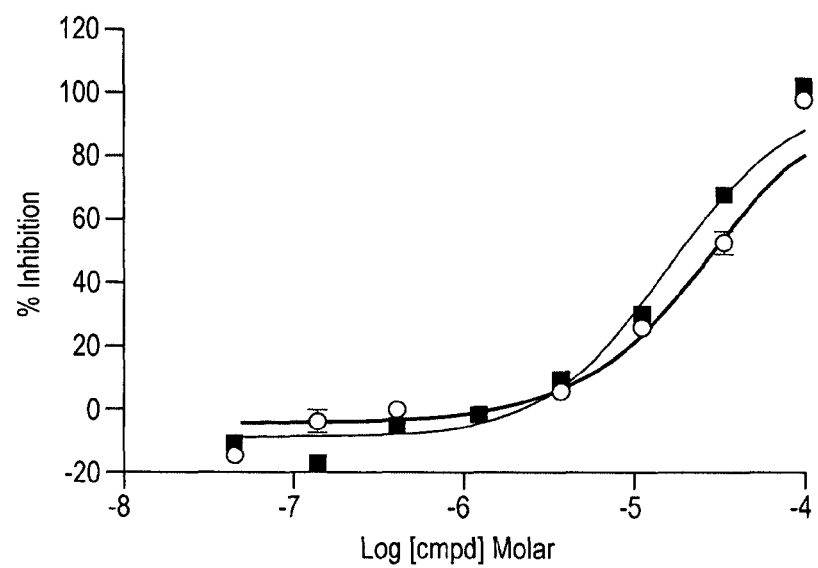
FIG. 10 shows inhibition of kynurenine production in A172 cells by compound LM10.
Figure 11:
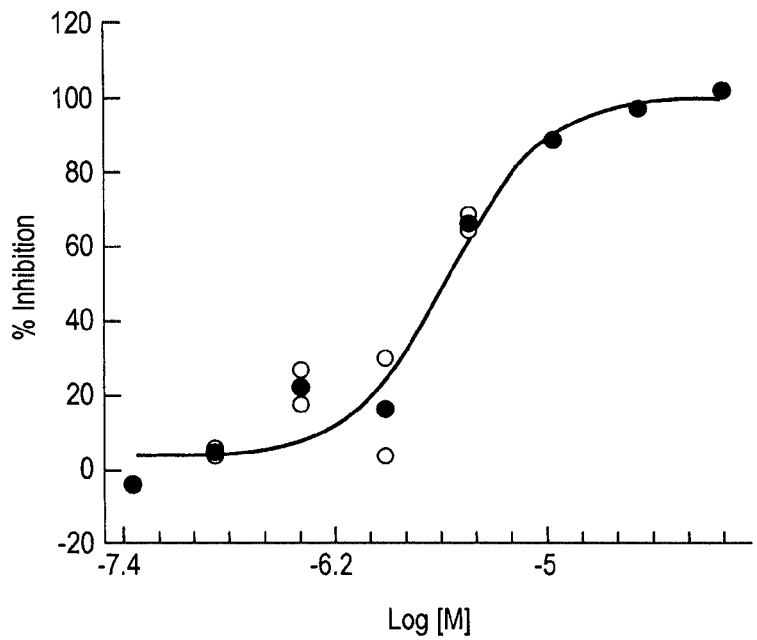
FIG. 11 shows inhibition of kynurenine production in SKOV3 cells by compound NewLink 1.
Figure 12:
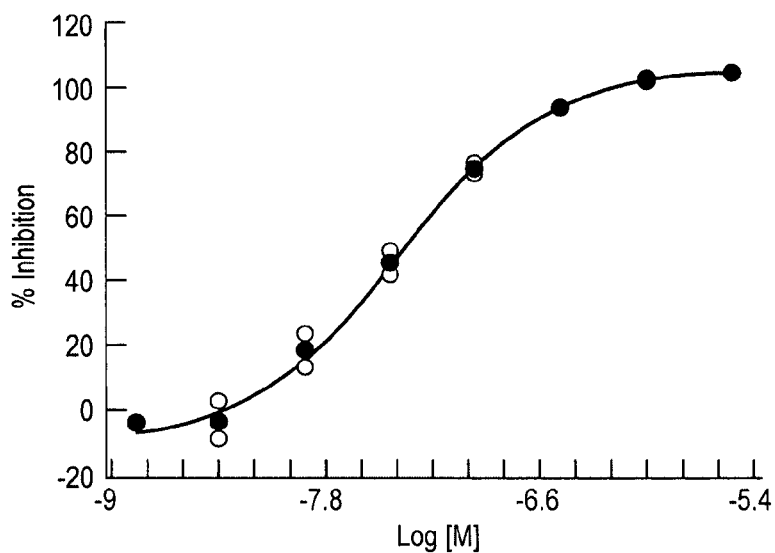
FIG. 12 shows inhibition of kynurenine production in SKOV3 cells by Incyte 1.

In two separate assays, 0.045 µg/µl of human IDO protein was pre-incubated for 10 min at RT with test compounds NewLink 1 and Incyte 1 in the presence of 50 mM $KPO_4$, pH 7.0, 0.5 mM EDTA, 0.5 mM EGTA, 0.05% Triton X-100, 20 mM ascorbate, 500 U/ml catalase, 10 µM methylene blue at RT in a 384 well plate. 0.05 µg/µl kynurenine formamidase (*drosophila*) and 45 µM L-tryptophan (L-Trp) were added and the assays were incubated at RT for 17 min. Assays were stopped and the level of kynurenine was determined by incubation with Ehrlich's reagent to a final concentration of 1.33% at RT for 5 min. Fluorescence intensity was read at 475 nm/530 nm. The results are depicted in FIG. 7 and FIG. 8 respectively.

Cell-Based Assays Measuring Kynurenine Production

In order to confirm the results of the screening method of the invention, cell-based assays were undertaken in respect of the exemplary compounds.

A172 human glioblastoma (ATCC) were grown in DMEM+2 mM L-glutamine medium (Invitrogen) supplemented with 10% foetal bovine serum (HyClone) and SK-OV-3 ovary adenocarcinoma (ATCC) cells were grown in McCoys 5A+L-glutamax medium (Invitrogen) supplemented with 15% foetal bovine serum (HyClone). On the day of assay, cells were detached using trypsin-EDTA (0.25% v/v Invitrogen), re-suspended in assay media (RPMI 1640 (phenol red free+L-glutamine) supplemented with 10% dialysed foetal bovine serum). A172 cells were seeded at 30K cells per well and SK-OV-3 cells at 40K cells per well into 96-well plates containing test samples/vehicle control together with 500 μM L-Trp. Cells were then incubated for 48 h at 37° C., 5% $CO_2$. IFNγ was also added at 500 ng/ml for the 48 h incubation in order to induce expression of IDO. Plates were then centrifuged (550 g for 10 min) and 50 μL supernatant were incubated for 5 min with 50 μl 2% Erhlich's reagent (2% w/v in 100% acetic acid). Kynurenine levels were then quantified by measuring absorbance at 490 nm.

The pIC50 values for the exemplar compounds at TDO and at IDO are shown in Table 1 and Table 2 respectively.

TABLE 1 pIC50 values for TDO inhibition determined for exemplar compounds

| Compound | hTDO biochemical assay pIC50 | A172 Kynurenine cell based assay pIC50 |
|---|---|---|
| 680C91 | 5.0 | 6.0 |
| LM10 | 5.1 | 4.7 |
| Incyte 1 | 5.6 | 5.0 |
| NewLink 1 | 6.3 | 4.9 |
| IOmet A | 5.2 | 6.8 |
| IOmet B | 5.4 | 5.8 |

TABLE 2 pIC50 values for IDO determined for exemplar compouds

| Compound | hIDO biochemical assay pIC50 | SKOV3 Kynurenine cell based assay pIC50 |
|---|---|---|
| NewLink 1 | 6.4 | 5.5 |
| Incyte 1 | 6.4 | 7.4 |
| IOmet A | <3.9 | <4.0 |
| IOmet B | <3.9 | <4.0 |

The data for the cell-based assays are depicted in more detail in FIGS. 9-12 respectively.

The Tables and Figures show that the screening method has been successful in identifying compounds showing strong TDO and IDO inhibitory function. The inhibitory function of screened compounds has been separately confirmed in the cell-based assays.

In summary, the methodology of the invention provides clear practical applicability for screening large libraries of organic molecules. The enzymatic coupling aspect of the methodology provides a practical solution to safely adapting the assay onto robotic and automation platforms and hence, enabling high-throughput screening. Crucially, this provides the opportunity to screen for modulators of TDO and IDO on an industrial scale. The high sensitivity of the assay provides accurate information on a wide range of activity, including weakly active hit compounds.

The invention claimed is:

1. A high-throughput coupled enzyme method of screening for a tryptophan-2,3-dioxygenase (TDO) inhibitor compound and/or an indoleamine-2,3-dioxygenase (IDO) inhibitor compound, which method comprises:
   (a) reacting tryptophan with isolated IDO and/or isolated TDO in the presence of a test compound to form N-formylkynurenine;
   (b) reacting N-formylkynurenine from step (a) with isolated kynurenine formamidase to form kynurenine; and
   (c) detecting the kynurenine produced in step (b) and determining whether the test compound is a TDO and/or an IDO inhibitor compound or not from the presence or absence or quantity of the detected kynurenine, wherein step (a) is conducted in the presence of a reducing system suitable for converting IDO and/or TDO from the $Fe^{3+}$ to the $Fe^{2+}$ state, and which does not prevent the formation of kynurenine in step (c).

2. A method according to claim 1, wherein the reducing system comprises a reducing agent and an electron transport agent.

3. A method according to claim 2, wherein the reducing agent is selected from ascorbic acid, TCEP and/or dithionite.

4. A method according to claim 2, wherein the electron transport agent comprises methylene blue.

5. A method according to claim 1, wherein the detection of kynurenine is carried out by direct absorbance or by fluorescence.

6. A method according to claim 5, wherein the absorbance wavelength is from 480-500 nm.

7. A method according to claim 1, wherein step (c) comprises a step of measuring the presence or absence or quantity of kynurenine by reacting the product of step (b) with Ehrlich's reagent and measuring the fluorescence intensity of the product.

8. A method according to claim 1, wherein the tryptophan comprises L-tryptophan.

9. A method according to claim 1, wherein the IDO comprises human IDO.

10. A method according to claim 1, wherein the IDO comprises recombinant IDO.

11. A method according to claim 1, wherein the TDO comprises human TDO.

12. A method according to claim 1, wherein the TDO comprises recombinant TDO.

13. A method according to claim 1, wherein the kynurenine formamidase comprises *drosophila* kynurenine formamidase.

14. A method according to claim 1, wherein the kynurenine formamidase comprises recombinant kynurenine formamidase.

15. A method for screening for an agent for treating a disease, a condition, and/or a disorder, which method comprises a method as defined in claim 1.

16. A method according to claim 15, wherein the disease condition and/or disorder is selected from: a cancer, an inflammatory condition, an infectious disease, a central nervous system disease or disorder, coronary heart disease, chronic renal failure, post anaesthesia cognitive dysfunction, a disease condition or disorder relating to female reproductive health, and cataracts, which compound is a compound as defined in any preceding claim.

17. A method according to claim 16, wherein the agent is an IDO inhibitor and the cancer is preferably a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, *Proteus* syndrome, and *Proteus*-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma), and preferably wherein the cancer is a cancer selected from acute myeloid leukemia (AML), a small-cell lung cancer, a melanoma, an ovarian cancer, a colorectal cancer, a pancreatic cancer, an endometrial cancer, and a skin papilloma.

18. A method according to claim 16, wherein the agent is a TDO inhibitor and the cancer is preferably a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, *Proteus* syndrome, and *Proteus*-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma), and preferably wherein the cancer is a cancer selected from a glioma, and a hepatocellular carcinoma.

19. A method according to claim 16, wherein the infectious disease is selected from a bacterial infection and a viral infection, preferably a gut infection, sepsis, and sepsis induced hypotension.

20. A method according to claim 16, wherein the central nervous system disease or disorder is selected from amyotrophic lateral sclerosis (AML), Huntington's disease, Alzheimer's disease, pain, a psychiatric disorder, multiple sclerosis, Parkinson's disease, and HIV related neurocognitive decline.

* * * * *